(12) United States Patent
Steinbach et al.

(10) Patent No.: US 10,365,097 B2
(45) Date of Patent: Jul. 30, 2019

(54) SONDE HAVING ORIENTATION COMPENSATION FOR IMPROVED DEPTH DETERMINATION

(71) Applicant: In-Situ, Inc., Fort Collins, CO (US)

(72) Inventors: Ashley Steinbach, Fort Collins, CO (US); Duane B. McKee, Fort Collins, CO (US)

(73) Assignee: IN-SITU, INC., Fort Collins, CO (US)

( * ) Notice: Subject to any disclaimer, the term of this patent is extended or adjusted under 35 U.S.C. 154(b) by 134 days.

(21) Appl. No.: 15/148,832

(22) Filed: May 6, 2016

(65) Prior Publication Data

US 2017/0176183 A1   Jun. 22, 2017

Related U.S. Application Data

(60) Provisional application No. 62/271,198, filed on Dec. 22, 2015.

(51) Int. Cl.
*G01B 21/18*   (2006.01)
*G01N 33/18*   (2006.01)

(52) U.S. Cl.
CPC ......... *G01B 21/18* (2013.01); *G01N 33/1886* (2013.01)

(58) Field of Classification Search
CPC ... G01N 21/532; G01N 33/1886; G01B 21/18
See application file for complete search history.

(56) References Cited

U.S. PATENT DOCUMENTS

| 5,099,920 A | 3/1992 | Warburton et al. |
| 5,259,452 A | 11/1993 | Wittrisch |
| 5,440,126 A | 8/1995 | Kemsley |
| D371,517 S | 7/1996 | Narayanan |

(Continued)

FOREIGN PATENT DOCUMENTS

| EP | 1851537 | 9/2013 |
| WO | WO2006/088829 | 8/2006 |
| WO | WO2014125457 | 8/2014 |

OTHER PUBLICATIONS

Final Rejection corresponding to U.S. Appl. No. 14/937,170, dated Mar. 2, 2017.

(Continued)

*Primary Examiner* — Elias Desta
(74) *Attorney, Agent, or Firm* — Leydig, Voit & Mayer, Ltd.

(57) ABSTRACT

Provided herein are sondes having a pressure sensor that is separated from active sensing portions of the other sonde sensor or sensors by a longitudinal distance along the sonde. The pressure sensor may be positioned in the base portion of the sonde, with removable sensors connected thereto with a sensor plane at a distal end of the sensors that measures any number of parameters associated with the liquid in which the sonde is immersed. An orientation sensor positioned in the base portion determines an orientation angle of the sonde that, in combination with the depth determined at the pressure sensor location by the pressure sensor, provides the ability to determine the actual depth of the sensor plane, irrespective of orientation angle. Accordingly, improved depth measurement is achieved, without having to confine placement of the pressure sensor at the sensor plane.

23 Claims, 5 Drawing Sheets

Depth in Practical Deployment

(56) References Cited

U.S. PATENT DOCUMENTS

| | | | |
|---|---|---|---|
| 5,596,193 | A | 1/1997 | Chutjian et al. |
| 5,820,416 | A | 10/1998 | Carmichael |
| D418,073 | S | 12/1999 | Kreutzer et al. |
| 6,157,029 | A | 12/2000 | Chutjian et al. |
| 6,234,019 | B1 | 5/2001 | Caldeira |
| 6,305,944 | B1 | 10/2001 | Henry et al. |
| 6,470,979 | B1 * | 10/2002 | Wentworth ............... E21B 7/06 175/320 |
| 6,677,861 | B1 | 1/2004 | Henry et al. |
| 6,779,383 | B2 | 8/2004 | Lizotte et al. |
| 6,798,347 | B2 | 9/2004 | Henry et al. |
| 6,928,864 | B1 | 8/2005 | Henry et al. |
| 6,938,506 | B2 | 9/2005 | Henry et al. |
| 6,943,686 | B2 | 9/2005 | Allen |
| 7,007,541 | B2 | 3/2006 | Henry et al. |
| 7,138,926 | B2 | 11/2006 | Henry et al. |
| 7,142,299 | B2 | 11/2006 | Tokhtuev et al. |
| 7,221,136 | B2 * | 5/2007 | Olsson ................... G01V 3/081 324/244 |
| 7,470,917 | B1 | 12/2008 | Hoang et al. |
| D616,314 | S | 5/2010 | Akomolede |
| 7,832,295 | B2 | 11/2010 | Rodriguez et al. |
| 7,900,528 | B2 | 3/2011 | Vincent |
| 8,429,952 | B1 | 4/2013 | Bringhurst et al. |
| 8,488,122 | B2 | 7/2013 | Dong et al. |
| 8,514,066 | B2 | 8/2013 | Harmon |
| 8,542,189 | B2 | 9/2013 | Milne et al. |
| 8,555,482 | B2 | 10/2013 | Metzger |
| 8,664,938 | B2 | 3/2014 | Palassis et al. |
| 8,797,523 | B2 | 8/2014 | Clark |
| D755,655 | S | 5/2016 | Scott et al. |
| 2002/0178805 | A1 * | 12/2002 | DiFoggio ................ E21B 47/10 73/152.55 |
| 2003/0117623 | A1 | 6/2003 | Tokhtuev et al. |
| 2003/0148637 | A1 | 8/2003 | Henry et al. |
| 2006/0179599 | A1 | 8/2006 | Miner et al. |
| 2007/0140921 | A1 | 6/2007 | Mitchell |
| 2008/0300821 | A1 | 12/2008 | Frank et al. |
| 2009/0158819 | A1 | 6/2009 | Vincent |
| 2010/0321046 | A1 | 12/2010 | Randall et al. |
| 2011/0005801 | A1 | 1/2011 | Olivier et al. |
| 2011/0023586 | A1 | 2/2011 | Leyer et al. |
| 2011/0273710 | A1 | 11/2011 | Dong et al. |
| 2012/0242993 | A1 | 9/2012 | Schick et al. |
| 2012/0262618 | A1 | 10/2012 | Weakly |
| 2012/0325018 | A1 | 12/2012 | Roth et al. |
| 2013/0008466 | A1 | 1/2013 | Karagöz et al. |
| 2013/0090789 | A1 | 4/2013 | DeDonato |
| 2014/0017143 | A1 | 1/2014 | Clark |
| 2016/0139046 | A1 | 5/2016 | Baltz et al. |
| 2016/0139070 | A1 | 5/2016 | Scott et al. |
| 2016/0139101 | A1 | 5/2016 | Scott et al. |
| 2016/0146777 | A1 | 5/2016 | McKee et al. |

OTHER PUBLICATIONS

International Search Report corresponding to International Patent Application No. PCT/US16/31268, dated Aug. 29, 2016.
Non-Final Rejection corresponding to U.S. Appl. No. 14/937,240, dated Feb. 9, 2017.
Non-Final Rejection corresponding to U.S. Appl. No. 14/937,170, dated Oct. 13, 2016.
Non-Final Rejection corresponding to U.S. Appl. No. 14/937,138, dated Oct. 20, 2016.
U.S. Appl. No. 29/558,419, filed Mar. 17, 2016, Scott et al.
U.S. Appl. No. 29/558,413, filed Mar. 17, 2016, Scott et al.
U.S. Appl. No. 29/558,414, filed Mar. 17, 2016, Scott et al.
U.S. Appl. No. 29/558,417, filed Mar. 17, 2016, Scott et al.
Sonde Wikipedia, accessed Nov. 4, 2015.
Teledyne Isco AQ700 Water Quality Multi-Parameter Sonde, 2 pages, Sep. 2013.
YSI EXO1 Multiparameter Sonde, http://www.ysi.com/productsdetail.php?EXO1-Water-Quality-Sonde-89, webpage publicly available at least as early as Oct. 2014.
YSI EXO2 Multiparameter Sonde, https://www.ysi.com/EXO2, webpage publicly available at least as early as Oct. 2014.
Hydrolab HL4 http://hydrolab.com/hydrolab-hl4-multiparameter-sonde/, webpage publicly available at least as early as May 6, 2014.
Ott Hydrolab DS5 http://www.ott.com/products/water-quality/hydrolab-ds5-multiparameter-data-sonde/, webpage publicly available at least as early as Oct. 2014.
In Situ TROLL 9500 Multiparameter Sonde, https://in-situ.com/products/water-quality-testing-equipment/troll-9500-multiparameter-sonde/, webpage publicly available at least as early as Apr. 1, 2015.
In Situ Aqua TROLL 600 Multiparameter Sonde, https://in-situ.com/products/water-quality-testing-equipment/aqua-troll-600-multiparameter-sonde/, webpage publicly available at least as early as Sep. 14, 2015.
In Situ AquaTROLL 600 Product Information, https://in-situ.com/blog/introducing-the-aqua-troll-600-water-quality-platform-2/, webpage publicly available at least as early as Sep. 21, 2015.
In Situ Water Quality Testing Equipment Products, https://in-situ.com/product-category/water-quality-testing-equipment/, webpage publicly available at least as early as Apr. 1, 2015.
Examiner's Report for corresponding CA Application No. 163113, dated Nov. 16, 2015, 3 pages.
6-Series Multiparameter Water Quality Sondes, YSI Environmental, dated Aug. 24, 2006, 14 pages.
International Search Report with Written Opinion corresponding to International Patent Application No. PCT/US2015/059925, dated Jan. 20, 2016, 8 pages.
International Search Report with Written Opinion corresponding to International Patent Application No. PCT/US2015/059920, dated Jan. 29, 2016, 7 pages.
International Search Report and Written Opinion corresponding to International Patent Application No. PCT/US2015/059918, dated Feb. 1, 2016, 8 pages.
International Search Report with Written Opinion corresponding to International Patent Application No. PCT/US2015/059939, dated Jan. 13, 2016, 9 pages.

* cited by examiner

SONDE HAVING ORIENTATION COMPENSATION FOR IMPROVED DEPTH DETERMINATION

CROSS-REFERENCE TO RELATED APPLICATIONS

This application claims the benefit of U.S. Provisional Patent Application No. 62/271,198 filed Dec. 22, 2015, which is specifically incorporated by reference to the extent not inconsistent herewith.

BACKGROUND OF INVENTION

Provided herein are compact sondes having a small diameter form factor and accurate depth measurement without sacrificing the number of water parameters capable of being measured by sensors arranged along a sensor plane.

In a small diameter submersible multiparameter sonde, space constraints and limitations can make it challenging to align all sensors to a common sensor plane. Although a pressure sensor used to measure depth is a good candidate to locate elsewhere on the sonde, challenges arise with such a configuration. For example, positioning a pressure sensor away from the common sensor plane can result in significant errors in determining the actual depth of the sensor plane as the sonde moves and orients in different directions, including non-vertical directions.

One method for determining actual depth of the sonde sensor plane is to add to the depth determined by the pressure sensor the corresponding separation distance between the sensor plane and the location of the pressure sensor. This provides an accurate depth determination, however, only for a sonde in the absolute vertical orientation. Failing to account for the deployment angle relative to vertical of the sonde can result in an inaccurate depth measurement and corresponding incorrect deployment depth of the sonde sensor plane. For example, if the sonde flips from a vertical to horizontal during use, the error in depth for such a method corresponds to the separation distance between the sensor plane and the pressure sensor. Similarly, consider a typical longitudinal separation distance between sensor plane and pressure sensor position ($D_s$) of 7.50 inches. If the orientation angle ($\theta$) changes 15° (from an expected 90° to 75°), the vertical separation distance between sensor plane and pressure sensor ($D_x$) changes from the expected 7.50 inches to 7.24 inches, an error of 0.26 inches. In a shallow water application, for example 20 feet, that error approaches the magnitude of the error of the pressure sensor, effectively doubling the error of the system. In the case where the sonde is laying horizontal on the bottom ($\theta=0°$), the error becomes 7.50 inches. In the extreme case where the end of the sonde is hung up on a rock and is completely upside down ($\theta=-90°$), the error in this example can jump to 15 inches of water pressure.

Accordingly, there is a need for the ability to accurately measure depth in sondes having a pressure sensor for depth measurement that is positioned away from the sensor plane. Such a configuration provides the functional benefit of being able to maximize the number of water parameters measured at the sensor plane by avoiding space otherwise occupied by the pressure sensor, while ensuring the sonde deployment depth is accurately determined at the sensor plane.

SUMMARY OF THE INVENTION

Provided herein are systems and methods of determining the actual depth of a sonde device, irrespective of sonde orientation, while removing the need of the pressure sensor to be aligned with other sensors in a common sensor plane. Small form-factor and diameter sondes, including those provided in U.S. patent application Ser. No. 14/937,138 titled "Submersible Multi-Parameter Sonde Having A High Sensor Form Factor Sensor" filed Nov. 10, 2015, provide a number of advantages over conventional sondes, including being able to have longer deployment times with an ability to clean the tightly fitted sensor plane formed from a plurality of individuals sensors. While such small-diameter and compact sondes provide a number of benefits, they are accordingly limited in the number of sensors that may be arranged at a common sensor surface and corresponding sensor plane. The systems and methods provided herein facilitate removal of a pressure sensor otherwise positioned at the common sensor plane, thereby freeing up space for other sensors.

In particular, provided herein are devices and methods where the pressure sensor is removed and spatially separated from the sensor plane formed by the other sensors of the sonde. In particular, the pressure sensor may be located within the sonde body, while the other sensors extend away from the body in a longitudinal direction, with the distal end of the sensor having the active sensing region forming the sensor plane. While pressure is an important physical property for measurement in typical sonde applications in order to obtain a depth measurement, a pressure sensor to measure depth merely needs to be in fluid communication with the body of the fluid being tested in order to operate. However, by moving the pressure sensor to a different position away from the other sensors in the sonde device, true depth measurement at the sensor plane is then estimated based on the distance between the pressure sensor and the sensor plane. Although at very large depths the percentage error in depth measurement may be small, the error becomes significant and substantial at smaller depths associated with shallower fluid applications, including groundwater applications. While there is no orientation-associated depth error for a sonde remaining in true correct vertical alignment, such an orientation is not realistic during actual use where there may be fluid motion disturbing the sonde and affecting orientation change during use. Examples include water currents, flowing water, or movement by the user deploying the sonde, including from a water-craft on the water surface, where there is deviation from vertical, such as at least 5°, 10°, 15° or more deviation from vertical. Accordingly, accurate depth measurement is challenging as the sonde tends to not remain consistently in a straight up and down configuration due to current in the water, movement at the surface such as being attached to a boat, ship or a person, touching debris or the bottom surface over which the fluid is located, or other interaction that perturbs sonde orientation.

In view of these limitations, there is a need for new sonde configurations which remove sensors from the crowded sensor plane that measures non-pressure fluid parameters, while still providing accurate and reliable depth information. Provided herein are systems and methods that remove the pressure sensor from the sensor plane and, instead, position the sensor in the sonde body along with an orientation sensor that allows for accurate calculation of depth, even when the sonde is not vertically aligned.

The systems and methods provided herein utilize an orientation sensor, such as an accelerometer, to determine the vertical orientation of the sonde in operation and then calculate an adjustment in the depth provided by a pressure sensor in the sonde body to accurately describe the depth of the sensor plane. These systems and methods allow for more sensors to be placed at the sensor plane in a compact small-diameter sonde. Along with any other physical parameters of interest, the pressure and depth may be recorded in an electronically-readable medium for future display or directly displayed, including to an electronic display or fixed in a physical medium (e.g., paper summary).

Provided is a method for determining actual immersion depth of a submersible sonde immersed in a fluid, the method comprising the steps of: measuring a pressure (P) with a pressure sensor of the submersible sonde submersed in a fluid, wherein the pressure sensor has a pressure sensor position in the submersible sonde; determining a fluid depth ($D_p$) at the lateral pressure sensor position based on the measured pressure (P); measuring an orientation angle (θ) of the submersible sonde immersed in a fluid, wherein the orientation angle is determined by a 3-axis accelerometer positioned in the submersible sonde; calculating a vertical distance ($D_x$) between a sensor plane of the submersible sonde and the pressure sensor position based on the determined orientation angle and a known separation distance ($D_s$) between the sensor plane and the pressure sensor position; and (e) determining the actual immersion depth (D) by summing $D_x$ and $D_p$. The liquid may be associated with any number of applications, including groundwater monitoring, aquifer characterization, hydraulic fracturing, aquaculture, mining, remediation, and surface water applications. With respect to the actual immersion depth, "determining" is used broadly to refer to the relevance of the true depth at which sensing occurs and includes practical use of the determined depth, including by recording and/or displaying of the determined actual immersion depth to a user.

In an embodiment, the orientation angle is expressed relative to a horizontal axis, so that $D_x = D_s \sin \theta_H$, or optionally, the orientation angle is expressed relative to a vertical axis, so that $D_x = D_s \cos \theta_v$, where the value of θ in the horizontal versus vertical definition is related by $90° = \theta_H + \theta_v$. $D_p$ may be determined according to the formula:

$$D_p = \frac{P}{\rho g} \quad (Eq. 1)$$

wherein P is the measured pressure, ρ is a density of the fluid in which the submersible sonde is submersed, and g is an acceleration due to gravity. ρ is known for the fluid with, for example, fresh water and salt water having a density of 1 g/cm³ and about 1.025 g/cm³, respectively, and g is defined by standard as 9.8 m/s² at the Earth's surface.

$D_p$ may be between 3 feet and 250 feet, $D_x$ may be between 3 feet and 250 feet; and/or $D_s$ may be between 4" and 36". θ, relative to a vertical axis, can vary from 0 (corresponding to absolute vertical in a correct orientation) to 180 (corresponding to absolute vertical in an incorrect or flipped upside down orientation). The fluid may comprise ground water, optionally, moving surface ground water, defined by an average speed of the water, or current, such as a time-varying current averaging more than about 0.5 m/s. As described herein, θ is simply a reflection of an offset angle, and so may be defined in various manners depending on the reference axis without affecting the methods and devices provided herein.

The orientation angle may vary with time and the sonde can provide a time-varying actual immersion depth. The method may further comprise the step of trolling the sonde from a boat positioned on a surface of the fluid. The systems and methods provided may be described in terms of having an improved depth measurement compared to conventional sondes without the orientation-dependent depth correction. For example, the improved depth measurement accuracy that may be at least 0.25 inches of water, or between 0.25 and 20 inches of water better than an equivalent sonde without the orientation compensation. This accuracy may be described as for a sensor orientation that moves from true vertical to horizontal, or from true vertical to upside-down vertical, at any orientation angle therebetween.

The orientation sensor may determine an orientation angle relative to each of three orthogonal axis (x, y and z) according to the formula:

$$\theta = \arctan \frac{g_x}{\sqrt{g_y^2 + g_z^2}} \quad (Eq. 2)$$

wherein $g_x$, $g_y$ and $g_z$ are orthogonal acceleration components and the orientation sensor is calibrated so that the x-axis is parallel to the vertical axis of the sonde. In embodiments, for example, the sonde is a multiparameter sonde having an outer diameter less than or equal to 20 cm, less than or equal to 10 cm, or less than or equal to 6 cm. This is a reflection that as diameters are larger, there is less of a concern as to being able to position a large number of sensors at a single sensor plane. In other words, for sondes of large diameter, such as above 50 cm, there can be sufficient room for the pressure sensor to also be positioned at the sensor plane so that actual measured pressure provides actual depth at the sensor plane. The methods and devices provided herein, however, are compatible with any size sonde, where the pressure sensor is positioned away from the sensor plane.

Also provided herein are sondes that can perform any of the methods described herein. For example, the sonde may comprise: (a) a base having a plurality of sensor receiving ports and a base interior volume; (b) a plurality of sensors, each sensor having a proximal end operably positioned in one of the sensor receiving ports and a distal end extending a longitudinal distance from the base, wherein the plurality of distal ends forms a sensor plane; In this manner, each sensor is connected to the base at a unique port. The sensors connected to and extending from the port are also referred herein as "longitudinally-extending" or "longitudinal" sensors (see, e.g., FIG. 2) having a longitudinal length, "L" between proximal and distal ends, to distinguish from sensors in the base. (c) a pressure sensor for measuring a pressure exerted by a fluid on the pressure sensor, the pressure sensor at least partially positioned in the base interior volume and separated from the sensor plane by a separation distance ($D_s$); (d) an orientation sensor positioned in the base interior volume configured to determine an orientation of the multiparameter sonde when the multiparameter sonde is immersed in a fluid; and (e) a central processing unit (CPU), in data communication with the pressure sensor and the orientation sensor, wherein the CPU is configured to calculate an actual submersion depth of the sensor plane from a pressure measured by the pressure sensor, an orientation angle determined from the orientation sensor, and $D_s$.

A plurality of sensors may extend from the base measure to measure two or more fluid parameters independently selected from the group consisting of: conductivity, dissolved oxygen (DO), oxygen-reduction potential (ORP), pH, turbidity, ion selective concentration, and temperature.

The sonde may comprise: (a) a base having a sensor receiving port and a base interior volume; (b) a sensor having a proximal end operably positioned in the sensor receiving port and a distal end extending a longitudinal distance from the base corresponding to a sensor plane; (c) a pressure sensor for measuring a pressure exerted by a fluid on the pressure sensor, the pressure sensor at least partially positioned in the base interior volume and separated from the sensor plane by a separation distance ($D_s$); (d) an orientation sensor positioned in the base interior volume configured to determine an orientation angle of the sonde when the sonde is immersed in a fluid; and (e) a central processing unit (CPU), in data communication with the pressure sensor and the orientation sensor, wherein the CPU is configured to calculate an actual submersion depth of the sensor plane from a pressure measured by the pressure sensor, the orientation angle determined from the orientation sensor, and $D_s$.

The sonde may be a multi-parameter sonde in that two or more parameters are measured at the sensor plane by two or more longitudinal sensors. The sonde, accordingly, may comprise a plurality of sensors and a plurality of sensor receiving ports, wherein each of the plurality of sensors are connected to a unique individual sensor receiving port, and the plurality of distal ends define the sensor plane. In an embodiment, the orientation sensor comprises a three-axis digital accelerometer. In an embodiment, for example, the sonde has a diameter less than or equal to 20 cm, a $D_s$ between 4" and 36", a total sensor length between 12" and 40", and/or a maximum submersion depth between 600 feet and 1300 feet.

The sonde may be further described in terms of the longitudinal sensors, such as a plurality of independent sensors each having a distal sensing surface and a proximal end, wherein each of the plurality of independent sensors comprises: (i) an inner corner edge; (ii) a pair of side surfaces extending from the inner corner edge and ending at an outer edge, wherein the side surface define a plane and the planes are separated from each other by a side angle; and (iii) an outer facing surface that connects the pair of side surfaces at the outer edge, thereby forming a three-sided sensor housing; wherein adjacent distal sensing surfaces substantially continuously contact each other to form a continuous distal sensing surface comprising the plurality of independent sensors.

Each of the three-sided sensor may be right-angled at a corner, such as at a corner edge, opposibly positioned relative to the outer facing surface. In this manner, the sonde may have four sensor receiving ports to correspondingly connect four sensors to the base, and each of the outer facing surfaces in combination form a combined outer surface that is circular in cross-section. There may be a tight-fit contact between adjacent sensor side walls, so that outer facing surfaces in combination with each other form a well-defined outer diameter, such as an outer diameter that is less than 6 cm.

Furthermore, to facilitate automated and reliable cleaning and anti-fouling, each of the sensors may comprise a notch at the right-angled corner and the notches in each of sensors in combination form a central orifice configured to receive a drive shaft to rotate a wiper over the sensing plane, including a double-sided wiper that keeps the sensor plane obstruction-free and another surface that is separated and opposibly faces the sensor plane, such as an inner-facing guard surface.

The sonde may further comprise: (i) a display electronically connected to the central processing unit (CPU); and (ii) a measurement subsystem in electronic contact with the CPU and that provides input to the CPU from the sensor; wherein the base comprises an at least partially transparent water-tight housing and the interior volume of the water tight-housing is a water-tight volume; wherein the CPU, display, orientation sensor and measurement subsystem are positioned in the water-tight volume; and wherein the orientation sensor is configured to detect a change in orientation or an exerted force to generate an input to the CPU and the CPU is configured to process the input and control an output display configuration of the display based on the input. In some embodiments, the sonde further comprises a plurality of sensors, wherein the measurement subsystem provides input to the CPU from the plurality of sensors. In embodiments, the output display corresponds to one or more of: sonde deployment readiness; watertight status of a port; operational status of data logging functions; a battery condition; external power connections; or readings from connected sensors.

Any of the systems and methods provided herein may have a multiparameter sonde with a diameter less than 10 cm, including any of the multiparameter sondes described in U.S. patent application Ser. No. 14/937,138 and Ser. No. 14/937,152, each filed Nov. 10, 2015. Other multiparameter sondes and any components thereof, that may be used with or in the instantly provided systems and methods are described in Ser. No. 14/937,170 and Ser. No. 14/937,240, also filed Nov. 10, 2015.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Sonde" refers to a water quality monitoring instrument. "Multiparameter" more particularly refers to a sonde having multiple independent separate sensors for providing multiple water parameter values at a sensor plane, wherein those parameters are in addition to pressure and sonde orientation angle.

"Independent sensors" refers to the ability to insert or remove a sensor without affecting other sensors. For example, one of the sensors may be removed and replaced with a sensor blank. Similarly, a user in the field may simply remove one independent sensor and replace it with another of the same or different sensor, without affecting the other sensors. "Sensor blank" refers to an equivalently shaped object that is used in place of a sensor. Such a blank is useful if the user does not need or have a sensor to connect to the base so as to fully fill the sensor guard.

The devices provided herein are compatible with a range of sensors, including sensors that measure conductivity, dissolved oxygen (DO), oxygen-reduction potential (ORP), pH, pressure, depth, level, turbidity, ion selective electrodes for various ions, such as nitrate, ammonium and chloride, and temperature.

"Sensor plane" refers to the position at which the sensor elements of the longitudinally-extending sensor(s) are located. This is the relevant true vertical distance from a fluid surface, such as the water surface in which the sonde is deployed. For embodiments where there are multiple sensors, the location of the sensor plane may be a defined location within the plurality of distal sensing ends, such as at the center of the distal sensing surface.

Unless defined otherwise, "substantially" refers to a value that is within at least 20%, within at least 10%, or within at least 5% of a desired or true value. Substantially, accordingly, includes a value that matches a desired value.

"Operably connected" refers to a configuration of elements, wherein an action or reaction of one element affects another element, but in a manner that preserves each element's functionality. For example, a sensor operably connected to a sonde base refers to the ability of the CPU in the sonde base to receive the output from the sensor for processing without adversely impacting the functionality of the base to provide a water-tight seal so as to prevent unwanted water entry into the housing volume of the base.

"Releasably connected" or "releasably connects" refers to a configuration of elements, wherein the elements can be temporarily and reliably connected to each other and, as desired, removed from each other without adversely impacting the functionality of other elements of the device.

"Data communication" refers to components that are electronically connected for transmission of electrical signals corresponding to data between the components. For example, a digital pressure sensor may output a digital signal to a CPU so that the CPU calculates a depth based on the digital output of the pressure sensor. Similarly, an orientation sensor in data communication with the CPU facilitates use of the orientation angle of the sonde to calculate an actual vertical separation distance between the pressure sensor and the sensor plane. The connection may be via wired connection or a wireless connection.

"Orientation sensor" refers to an accelerometer or similar device that can provide an output dependent on the device's orientation. For example, by measuring acceleration forces in each of three orthogonal directions, the device can determine orientation. Examples include devices that have three orthogonally arranged one-axis accelerometers, each producing a signal corresponding to acceleration in an x-, y- or z-direction. Any of the sensors provided herein may have a digital output that is provided to a CPU for desired processing. The CPU may be within the sonde base. Alternatively, the data may be provided to an external CPU, such as via a wireless connection to a CPU of a handheld device or within a computer that is physically separate from the sonde base.

"Measurement subsystem" refers to those conventional electronics associated with sondes known in the art, such as standard electrical circuits that provide power, communicate with sensors, and the like. The electrical circuits may be in the form of printed circuit boards, chips, processors, with associated resistors, capacitors, switches, diodes, transistors and other basic electronic components to achieve the desired circuit, power, communication connections and functionality.

"Moving surface water" refers to water that is flowing in such a manner as making substantial deviation of the sonde from true vertical likely. In an aspect, moving water refers to water motion resulting in at least temporary sonde angle relative to vertical that is greater than 5°, greater than 10°, greater than 15°, or greater than 20°.

Example 1: Sonde with Pressure Sensor in the Body Separated from a Sensor Plane

Figure 1:
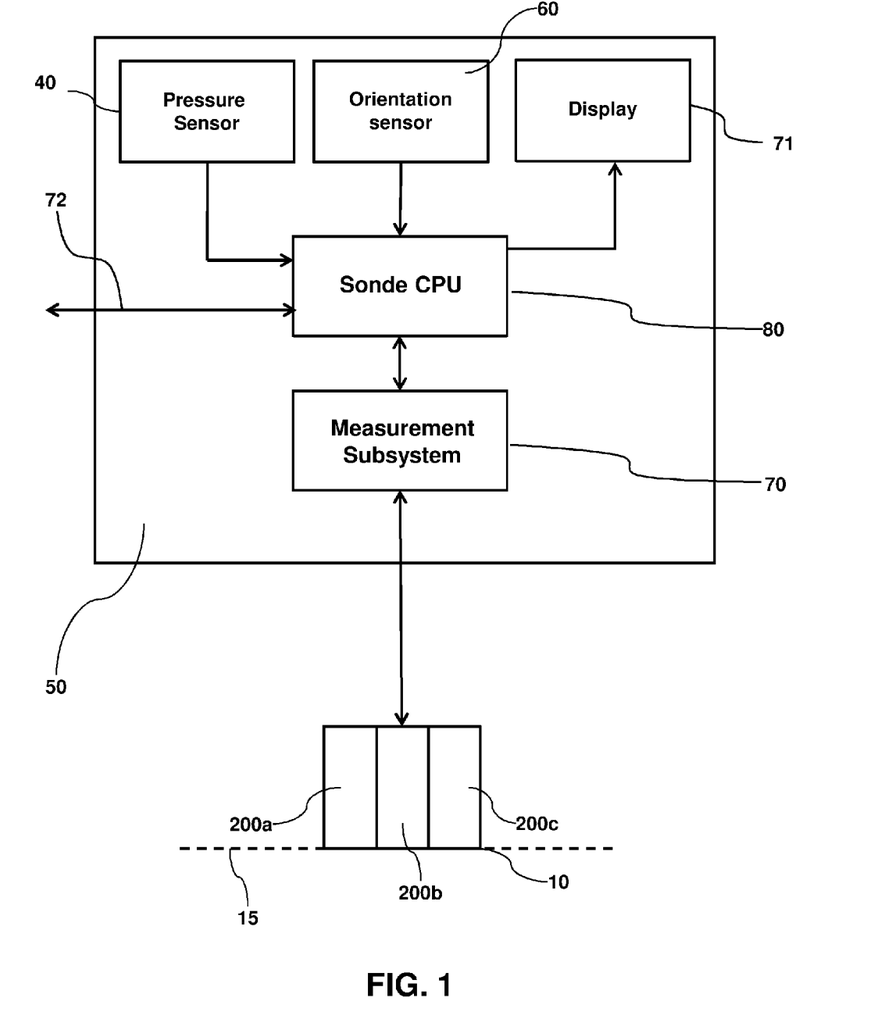
FIG. 1 is a schematic illustration of a sonde showing multiple sensors in data communication with the sonde base containing a central processing unit, a pressure sensor, and orientation sensor.

FIG. 1 provides a block diagram of a sonde with the pressure sensor 40 in the base 50 of the sonde to allow for additional sensors 200abc, with each distal end 10 of the sensor together forming the sensor plane 15 along the distal sensing surface. To distinguish from sensors 40 60 in the sonde base 50, sensors 200a 200b 200c are also referred herein as longitudinally-extending or longitudinal sensor to emphasize the sensor plane 15 separated relative to the base. The sonde base 50 may contain a pressure sensor 40 and an orientation sensor 60. The base 50 is operably connected to at least one sensor, here represented by three sensors as 200a, 200b, and 200c. The three sensors form a sensor plane 15 as indicated by the dashed line along the distal sensing end 10 of the sensors. The sensors 200abc, the pressure sensor 40, and the orientation sensor 60 all provide data to a central processing unit (CPU) 80, optionally this data may be stored and transmitted through a measurement subsystem 70. The central processing unit 80 calculates the depth of the sensor plane from pressure-dependent output from the pressure sensor 40, the orientation angle from the orientation sensor 60, and the constant geometric parameters of the sonde, such as distance between the pressure sensor 40 and the sensor plane 15. Additionally, the system may include an optional display 71 and a data output 72. The sonde, including the sonde sensors and/or sonde base, correspond to any of those described in U.S. patent application Ser. No. 14/937,138 (titled SUBMERSIBLE MULTI-PARAMETER SONDE HAVING A HIGH SENSOR FORM FACTOR SENSOR); Ser. No. 14/937,152 (titled: INTEGRATED USER INTERFACE FOR STATUS AND CONTROL OF A SUBMERSIBLE MULTI-PARAMETER SONDE); Ser. No. 14/937,170 (titled: CLEANABLE FLAT-FACED CONDUCTIVITY SENSOR); and Ser. No. 14/937,240 (titled: COMPACT SENSOR FOR MEASURING TURBIDITY OR FLUORESCENCE IN A FLUID SAMPLE), each filed Nov. 10, 2015, and each specifically incorporated by reference herein.

Figure 2:
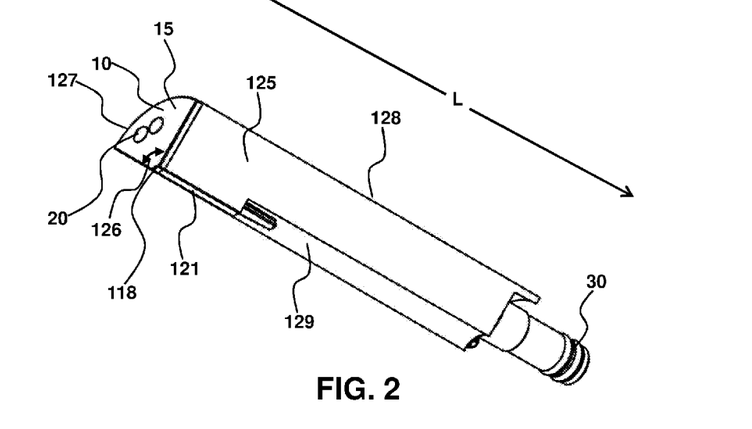
FIG. 2 illustrates an individual sensor that may be attached to the sonde base, with the distal sensing end that corresponds to a sensor plane.

An example of a longitudinal sensor for the measurement of a fluid parameter is provided in FIG. 2. The distal end 10 extends longitudinally from the base of the sonde, which may be connected to a receiving port 51 in the base 50 (see, e.g., FIG. 3) by a connection port at the proximal end 30 of the sensor. Sensor plane 15 then corresponds to the distal end 10. When multiple sensors are connected into the base, a single sensor plane is defined by each of the distal ends 10 in combination. The sensor contains at least one sensing element 20 at distal end 10 to measure a fluid parameter such as conductivity, dissolved oxygen, oxygen-reduction potential, pH, turbidity, ion selectivity and/or temperature.

The longitudinal sensor of FIG. 2 illustrates inner corner edge 118 from which side surfaces 125 extend. For clarity, only one of the pair of side surface 125 is illustrated, with the other side separated from the illustrated side surface 125 by side angle 126, illustrated with double ended arrow. Outer facing surface 127 connects the pair of side surfaces 125 to form the three-sided sensor housing 128. Illustrated in FIG. 4 are four distal sensing surfaces that together substantially and continuously contact each other to form a continuous distal sensing surface. This type of contact refers to, for example, a tight-fit connection such that unwanted biological growth leading to sensor fouling is prevented, or at least substantially hindered, so that over the deployment lifetime of the sonde adverse functional impact on the sensors is avoided. For example, the separation distance between surfaces described as in substantial and continuous contact with each other may be described as, at a maximum in any location, less than 2 mm, less than 1 mm, or less than 0.5 mm from each other. As illustrated, angle 126 may be right-angled, so as to accommodate a connection of four longitudinal sensors to the base. Notch 121 may accommodate a drive shaft 119 (FIG. 4), with another notch 129 to accommodate reliable connection of each of the sensors to a central support extending from central support port 52 (FIG. 3).

Figure 3:
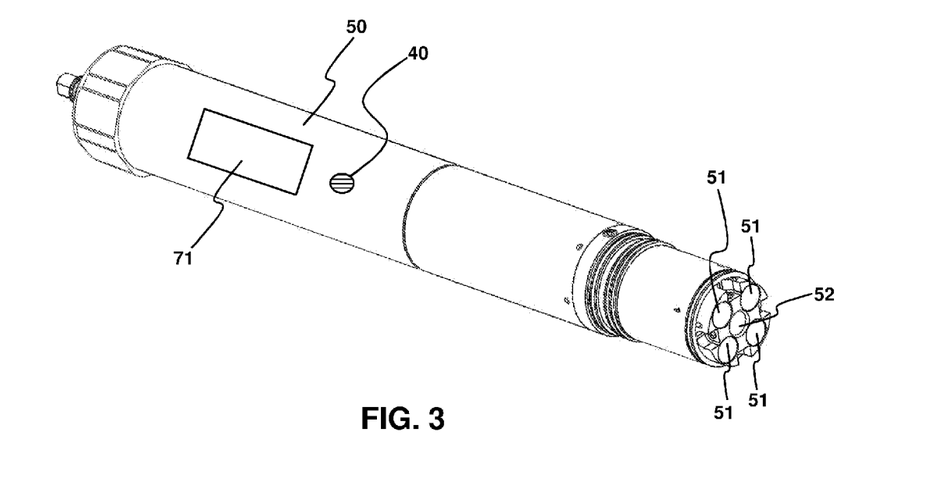
FIG. 3 illustrates a sonde base that houses a pressure sensor and an orientation sensor, with sensor receiving ports for operably connecting individual sensors, including a sensor illustrated in FIG. 2.
Figure 4:
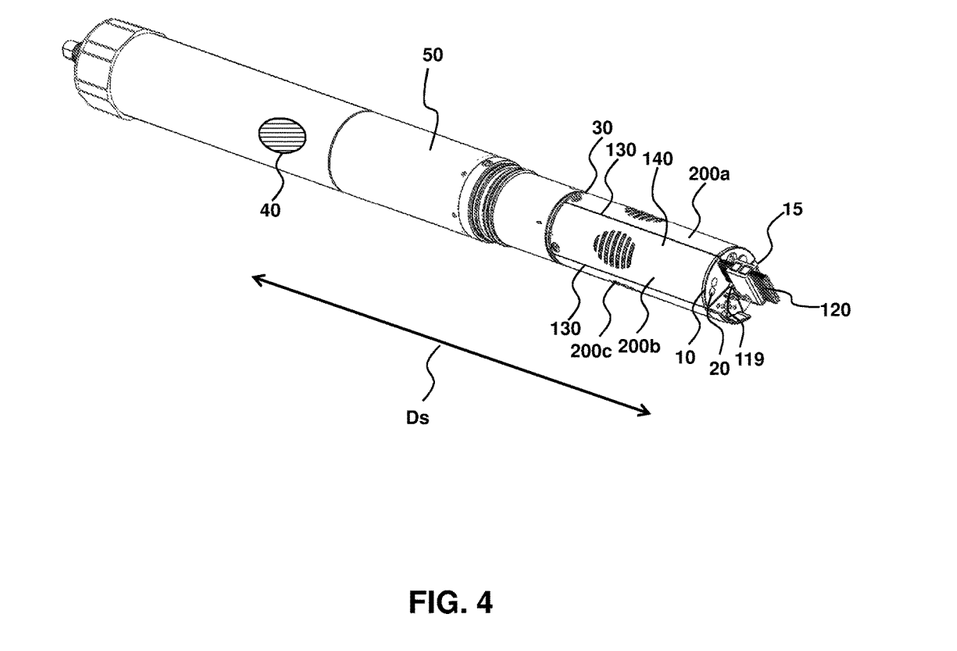
FIG. 4 illustrates a sonde in which four sensors are removably attached to the base, with the four distal sensing surface that form a sensor plane that is separated from the pressure sensor by separation distance $D_s$, and with a wiper for cleaning the sensor plane surface.

The base 50 of the sonde in which the sensors are connected is illustrated in FIG. 3. The base 50 has an interior volume containing a pressure sensor 40 and an orientation sensor, such as a three-axis accelerometer. At one end of the base is a plurality of sensor receiving ports 51 which provide a connection to sensors at their proximal ends 30. The base 50 may further comprise a display portion 71 for indicating sonde and sensor status and a central support port 52 to operably connect a central support and attendant drive shaft extending therefrom, with an attendant tight-fit connection between sensors having a well-defined sensor plane 15. FIG. 4 shows the base 50 connected to several sensors 200a, 200b, and 200c, with each sensor further illustrated in FIG. 2. By using sensors of similar longitudinal length, L, the distal ends 10 of the sensors and the probes 20 are aligned in a sensor plane 15 and have defined separation distance ($D_s$) along the sonde from pressure sensor 40. Also illustrated is a wiper 120 connected to a drive shaft 119 that extends from a central orifice defined by notches 121 at the inner corner edge 118 (see FIG. 2).

Example 2: Sonde in a Vertical Orientation

Figure 5:
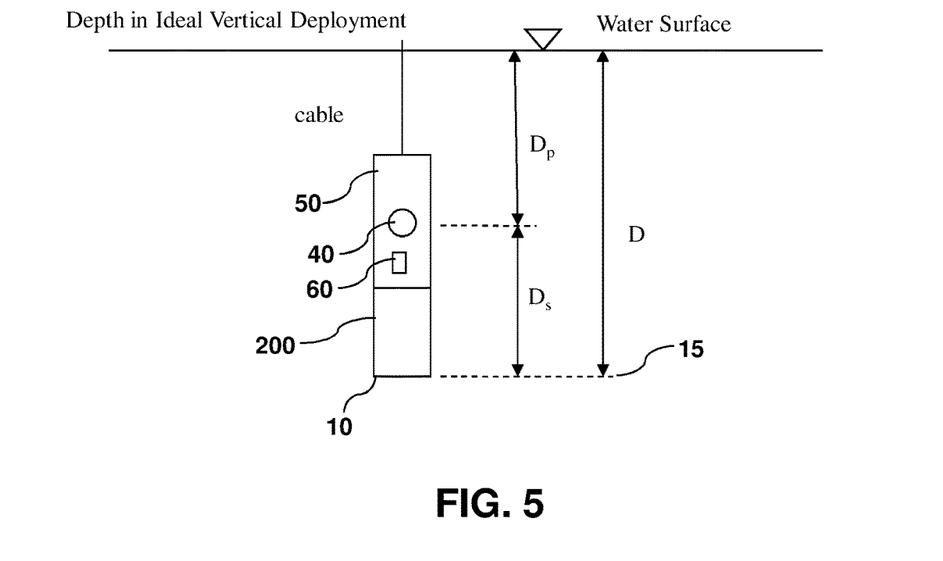
FIG. 5 provides the calculation of the depth of the sensor plane when the sonde is vertically aligned.

In ideal conditions, the sonde may be deployed such that it is perpendicular to the surface of the water and the base and sensor units are vertically aligned as illustrated in FIG. 5. In these conditions, determining the actual depth, D, of the sensor plane is straightforward. The pressure sensor 40 uses hydrostatic pressure to determine its depth relative to the water surface, $D_p$. Because the base and sensors are vertically aligned, the depth of the sensor plane with respect to the depth of the pressure sensor, Ds, is merely the length of the sensors 200 plus the length of the base between the pressure sensor 40 and the connection point between the sensor and the base. Thus, the depth of the sensor plane D is merely the sum of $D_p$ and $D_s$. As desired, pressure and depth may be determined from each other, such as by the hydrostatic equation for pressure, P=ρgh, where ρ is fluid density, g is the acceleration due to gravity, and h is the fluid depth.

Example 3: Sonde in an Offset-Orientation During Use

Figure 6:
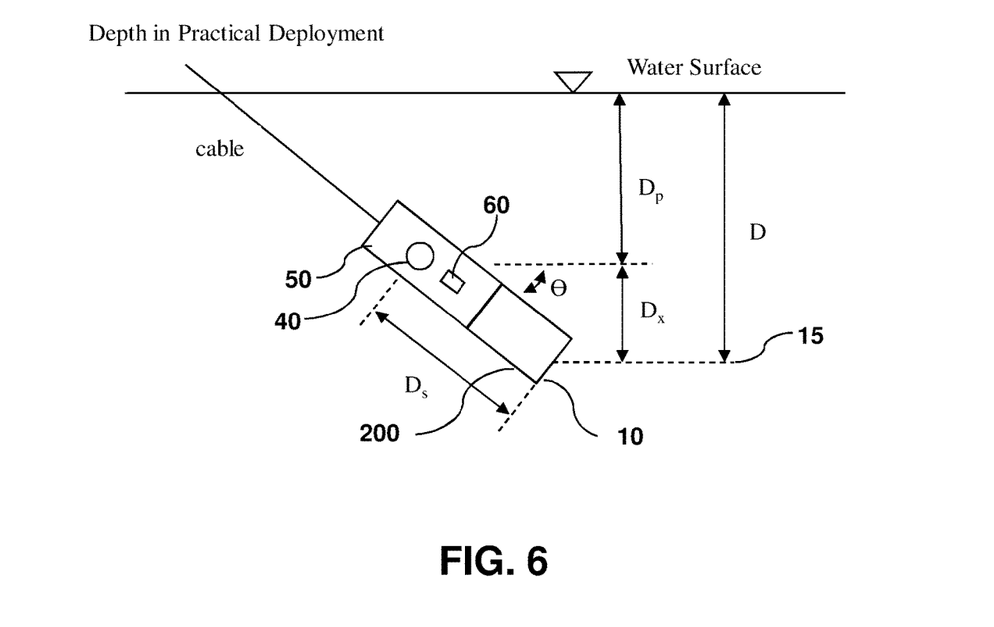
FIG. 6 provides the calculation of the depth of the sensor plane when the sonde is not vertically aligned.

In practical deployment, the sonde is often not in perfect vertical alignment due to external factors such as water current, trolling along the water surface, such as by a moving boat, touching the bottom surface, or protrusions from the bottom surface. FIG. 6 illustrates a sonde that is deployed at an angle θ≠90°, whereas in FIG. 5 θ=90°. In this situation, adding $D_p$ and $D_s$ no longer accurately provides the depth of the sensor plane. Instead, the orientation angle, θ, is necessary to calculate the actual depth which may be determined using an orientation sensor 60, for example, a digital three-axis accelerometer.

In this situation, the actual depth of the sensor plane, D, is defined by the relationship $D_p+D_x$ where $D_x=D_s \sin θ$, so that in FIG. 5, for θ=90° $D_x=D_s$, whereas in FIG. 6, $D_x≠D_s$. The orientation angle, θ, can be measured with an orientation sensor (60), such as a three-axis accelerometer, so that the actual depth of the sonde sensor plane (15) is provided by: $D_p+D_s \sin θ$, with each of those variable either known ($D_s$) or measured (pressure sensor 40 providing $D_p$, orientation sensor 60 providing θ). For a three-axis accelerometer, θ is determined by (Eq. 2):

$$θ = \arctan \frac{g_x}{\sqrt{g_y^2 + g_z^2}}$$

where $g_x$, $g_y$, and $g_z$ are orthogonal acceleration components in the x, y and z axis, respectively, and the orientation sensor is calibrated to a vertically aligned sonde. The orientation sensor may provide continuous orientation data, allowing the depth and pressure to be measured as a function of time. Of course, similar determinations may be made for θ defined relative to another axis, such as a horizontal axis or any other axis, as desired.

Figure 7:
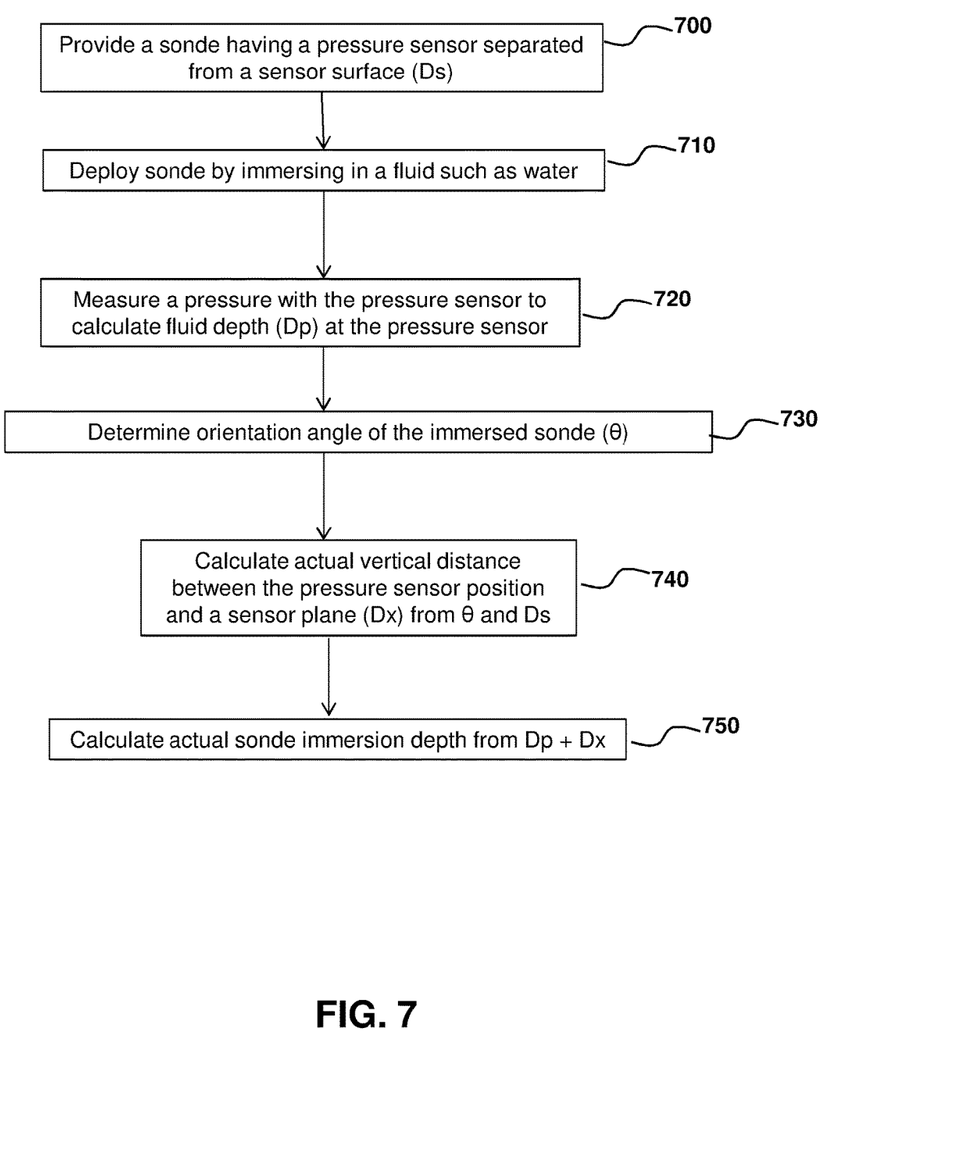
FIG. 7 provides a flow chart for a method of calculating actual immersion depth of a sensor plane.

FIG. 7 is a process flow summary of a method for determining actual depth for a sonde having any orientation angle. Step 700 summarizes any of the sondes described herein is provided with the pressure sensor separated by a distance $D_s$ from the sensing elements located on each of the other sensor distal sensing surfaces. The sonde is deployed in step 710, with the relevant fluid depending on the application of interest. As discussed herein, the fluid may be ground water or surface water. The pressure sensor measures pressure and, therefore, an attendant depth 720. In step 730, the orientation angle is determined. From these parameters, actual vertical distance between pressure sensor and sensor surface is determined, irrespective of orientation angle 740. The actual immersion depth, that is the distance of the sensor plane from the surface of the liquid, can be determined as illustrated in step 750.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, an angle range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents, publications and applications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:
1. A method for determining an actual immersion depth of a submersible sonde immersed in a fluid, the method comprising the steps of:
  immersing the submersible sonde in fluid, wherein the submersible sonde comprises:
    a base having a sensor receiving port and a base interior volume, wherein the sensor has a proximal end operably positioned in the sensor receiving port and a distal end extending a longitudinal distance from the base, the distal end of the sensor having an active sensing region forming a sensor plane;
    a pressure sensor at least partially positioned in the base interior volume, wherein a pressure sensor position is separated from the sensor plane by a separation distance ($D_s$), and wherein the pressure sensor has a lateral pressure sensor position in the submersible sonde;
    an orientation sensor positioned in the base interior volume; and
    a central processing unit (CPU) in data communication with the pressure sensor and the orientation sensor;
  measuring a pressure (P) with the pressure sensor of the submersible sonde submersed in the fluid;
  determining, by the CPU and based on the measured P, a fluid depth ($D_p$) at the lateral pressure sensor position, the $D_p$ defining a true vertical distance of the pressure sensor position from a surface of the fluid;
  measuring, by the orientation sensor, an orientation angle ($\theta$) of the submersible sonde immersed in a fluid, $\theta$ defining an angular displacement of the submersible sonde from a true vertical alignment of the submersible sonde;
  calculating, by the CPU and based on $D_s$ and based on the measured time-varying $\theta$, a vertical distance ($D_x$) between the sensor plane and the pressure sensor position; and
  determining the actual immersion depth (D) by summing $D_x$ and $D_p$, the D defining a true vertical distance of the sensor plane from the fluid surface.

2. The method of claim 1, wherein the orientation angle is expressed relative to a horizontal axis, so that $D_x = D_s \sin \theta$.

3. The method of claim 1, wherein the orientation angle is expressed relative to a vertical axis, so that $D_x = D_s \cos \theta$.

4. The method of claim 1, wherein $D_p$ is determined according to the formula:

$$D_p = \frac{P}{\rho g}$$

wherein P is the pressure measured by the pressure sensor, $\rho$ is a density of the fluid in which the submersible sonde is submersed, and g is an acceleration due to gravity.

5. The method of claim 1, wherein:
$D_p$ between 3 feet (0.9 m) and 250 feet (76 m);
$D_x$ between 3 feet (0.9 m) and 250 feet (76 m); and
$D_s$ between 4" (0.1 m) and 36" (0.9 m).

6. The method of claim 1, wherein θ, relative to a vertical axis, can vary from 0°, corresponding to absolute vertical in a correct orientation, to 180°, corresponding to absolute vertical in an incorrect or flipped upside down orientation.

7. The method of claim 1, wherein the fluid comprises groundwater.

8. The method of claim 7, wherein the fluid groundwater comprises moving surface water with an average speed that is greater than or equal to 0.5 m/s.

9. The method of claim 1, wherein during use the orientation angle varies with time, the method further comprising the step of displaying or recording in a physical medium a time-varying actual immersion depth.

10. The method of claim 1, further comprising the step of trolling the sonde from a boat positioned on a surface of the fluid.

11. The method of claim 1, having an improved depth measurement accuracy that is at least within 0.25 inches (0.635 cm) of water of actual depth.

12. The method of claim 1, wherein the orientation sensor determines an orientation angle relative to each of three orthogonal axis (x, y and z) according to the formula:

$$\theta = \arctan \frac{g_x}{\sqrt{g_y^2 + g_z^2}}$$

wherein $g_x$, $g_y$ and $g_z$ are orthogonal acceleration components and the orientation sensor is calibrated so that the x-axis is parallel to the vertical axis of the sonde, and the orientation sensor comprises a three-axis accelerometer.

13. The method of claim 1, wherein the sonde is a multiparameter sonde configured to receive at least four individual sensors, each of the at least four individual sensors having a distal sensing end that forms the sensor plane having a continuous distal sensing surface, wherein the multiparameter sonde has an outer diameter less than or equal to 6 cm.

14. The method of claim 13, wherein the multiparameter sonde comprises:
the base having a plurality of sensor receiving ports;
a plurality of sensors, each sensor having the proximal end operably positioned in one of said plurality of sensor receiving ports and the distal end extending the longitudinal distance from said base, wherein said plurality of distal ends forms said sensor plane; and the orientation sensor configured to determine an orientation of said multiparameter sonde when said multiparameter sonde is immersed in the fluid.

15. The method of claim 14, wherein the plurality of sensors extending from the base measure two or more fluid parameters selected from the group consisting of:
conductivity, dissolved oxygen (DO), oxygen-reduction potential (ORP), pH, turbidity, ion selective concentration, and temperature.

16. A sonde comprising:
a base having a sensor receiving port and a base interior volume;
a sensor having a proximal end operably positioned in said sensor receiving port and a distal end extending a longitudinal distance from said base, the distal end of the sensor having an active sensing region forming to a sensor plane;
a pressure sensor for measuring a pressure exerted by a fluid on said pressure sensor, said pressure sensor at least partially positioned in said base interior volume and separated from said sensor plane by a separation distance ($D_s$), wherein the pressure sensor has a pressure sensor position in the sonde;
an orientation sensor positioned in said base interior volume configured to measure an orientation angle of said sonde when said sonde is immersed in a fluid, the orientation angle defining an angular displacement of said sonde from a true vertical alignment of said sonde; and
a central processing unit (CPU), in data communication with said pressure sensor and said orientation sensor, wherein said CPU is configured to:
determine, based on the measured pressure, a fluid depth ($D_p$) at the pressure sensor position, the determined fluid depth defining a true vertical distance of the pressure sensor position from a surface of the fluid;
calculate, based on $D_s$ and based on the orientation angle, a vertical distance ($D_x$) between said sensor plane and the pressure sensor position;
determine an actual immersion depth of the sensor plane (D) by summing $D_x$ and $D_p$.

17. The sonde of claim 16, comprising a plurality of sensors and a plurality of sensor receiving ports, wherein each of said plurality of sensors is connected to a unique individual sensor receiving port, and said plurality of distal ends define said sensor plane, and wherein the CPU is configured to display the D of the active sensing region to a user deploying the sonde, or record the D of the active sensing region in a physical medium.

18. The sonde of claim 16, wherein said orientation sensor comprises a three-axis digital accelerometer.

19. The sonde of claim 16, having one or more of:
an outer diameter less than or equal to 20 cm;
$D_s$ between 4" (0.1 m) and 36" (0.9 m);
a total sensor length between 12" (0.3 m) and 40" (1.0 m); and
a maximum submersion depth between 600 feet (183 m) and 1300 feet (396 m).

20. The sonde of claim 17, wherein each of the plurality of sensors connected to a receiving port comprises:
an inner corner edge;
a pair of side surfaces extending from the inner corner edge and ending at an outer edge, wherein each of the side surfaces define a plane and the planes are separated from each other by a side angle;

an outer facing surface that connects the pair of side surfaces at the outer edge, thereby forming a three-sided sensor housing; and wherein adjacent distal sensing surfaces substantially continuously contact each other to form a continuous distal sensing surface comprising the plurality of sensors.

21. The sonde of claim 20, wherein each three-sided sensor is right-angled at a corner opposibly positioned relative to the outer facing surface.

22. The sonde of claim 21, having four sensor receiving ports to connect four sensors to the base, and each of the outer facing surfaces in combination form a combined outer surface that is circular in cross-section with an outer diameter that is less than 6 cm.

23. The sonde of claim 22, wherein each of the sensors comprise a notch at the right-angled corner and the notches in each of sensors in combination form a central orifice configured to receive a drive shaft to rotate a wiper over the sensing plane.

* * * * *